US009409164B2

United States Patent
Tawfik et al.

(10) Patent No.: US 9,409,164 B2
(45) Date of Patent: Aug. 9, 2016

(54) TRAY FOR TISSUE BIOPSY SAMPLES, METHODS OF MAKING, AND METHODS OF USING THEREOF

(75) Inventors: Ossama Tawfik, Leawood, KS (US); Swaran Jain, Lansing, KS (US); Maged Fanous, Overland, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 13/641,859

(22) PCT Filed: Apr. 18, 2011

(86) PCT No.: PCT/US2011/032861
§ 371 (c)(1),
(2), (4) Date: Jan. 2, 2013

(87) PCT Pub. No.: WO2011/133453
PCT Pub. Date: Oct. 27, 2011

(65) Prior Publication Data
US 2013/0108523 A1    May 2, 2013

Related U.S. Application Data

(60) Provisional application No. 61/325,721, filed on Apr. 19, 2010.

(51) Int. Cl.
*B01L 3/00* (2006.01)
*G01N 1/36* (2006.01)

(52) U.S. Cl.
CPC .. *B01L 3/502* (2013.01); *G01N 1/36* (2013.01)

(58) Field of Classification Search
CPC ................. A61B 2019/5238; G01N 33/4833
USPC ................................ 422/50, 500–503, 536
See application file for complete search history.

(56) References Cited

U.S. PATENT DOCUMENTS

| | | | |
|---|---|---|---|
| 4,120,547 A | | 10/1978 | Price et al. |
| 4,837,795 A | * | 6/1989 | Garrigus ................. 378/180 |
| 4,901,410 A | | 2/1990 | Fischer et al. |
| 5,609,827 A | * | 3/1997 | Russell et al. ........... 422/559 |
| 6,017,476 A | * | 1/2000 | Renshaw ................. 264/158 |
| 6,797,928 B2 | * | 9/2004 | Giberson et al. ........ 219/679 |
| 2006/0169719 A1 | | 8/2006 | Bui |
| 2008/0195066 A1 | | 8/2008 | Speeg et al. |
| 2009/0112118 A1 | | 4/2009 | Quick, Jr. et al. |

FOREIGN PATENT DOCUMENTS

| | | |
|---|---|---|
| CH | 700738 A2 * | 12/1978 |
| EP | 1736104 | 12/2006 |
| GB | 2453320 * | 4/2009 |

OTHER PUBLICATIONS

PCT/US2011/032861, Dec. 21, 2011, International search Report and Written Opinion.

* cited by examiner

*Primary Examiner* — Jyoti Nagpaul
(74) *Attorney, Agent, or Firm* — Workman Nydegger

(57) ABSTRACT

A tissue tray for collecting and organizing tissue biopsy samples as they are analyzed and prepared for histological analysis and other analyses. A tissue tray includes an upper surface and a bottom surface, at least one compartment formed in the upper surface of the tray configured to receive tissue and having one or more fluid conduits passing between openings in the upper and bottom surfaces, and at least one marker configured to indicate the orientation of the tray such that the tray is in the same orientation during radiological analysis and pathological analysis. Methods for fabricating the tray and methods for using the tray are also disclosed herein.

20 Claims, 8 Drawing Sheets

TRAY FOR TISSUE BIOPSY SAMPLES, METHODS OF MAKING, AND METHODS OF USING THEREOF

CROSS-REFERENCE TO RELATED APPLICATIONS

This application is a U.S. Nationalization of PCT Application Number PCT/US2011/032861, filed on Apr. 18, 2011, entitled "TRAY FOR TISSUE BIOPSY SAMPLES, METHODS OF MAKING, AND METHODS OF USING THEREOF," which claims the benefit of U.S. Provisional application 61/325,721 filed Apr. 19, 2010, titled "THE RAD/PATH TISSUE TRAY", which are incorporated herein by reference in their entireties.

BACKGROUND

Breast cancer is the most common malignancy in women accounting for about 30% of all tumors and is the second most lethal tumor in women, representing 16% of all deaths. This malignancy can occur at any age, but is unusual under 25 years. The peak incidence is between 45-60 years, with an occurrence rate of 1 in 232 in the fourth decade to 1 in 29 in the seventh decade. The frequency is increasing, particularly in younger age groups. In the Western Hemisphere, the lifetime risk for women is 1:12. It is 200 times more common in women than in men.

During the past three decades the introduction of screening mammography and other imaging modalities have brought about a greater knowledge and awareness of the characteristics of early breast cancer. Studies have shown that core needle biopsy (CNB) procedure is at least as accurate as open surgical biopsy in establishing definite diagnosis in mammographically suspicious lesions. The technique has gained popularity due to its accuracy, expedience, and practicality and is relatively inexpensive. CNBs of the breast are now considered to be the method of choice for the initial workup of mammographically suspicious breast lesions in many institutions. They have been shown to be highly sensitive and specific techniques for the management of patients with mammographically palpable and non-palpable abnormalities. Patients undergo stereotactic needle biopsy with commercially available vacuum-assisted percutaneous biopsy equipment using 8- or 11-gauge probe size (Mammotome, Biopsy Medical/Ethicon Endo-Surgery, Cincinnati, Ohio) or 9-gauge probe size (ATEC Breast Biopsy System, Suros Surgical Systems, Indianapolis, Ind.). Usually 3 to 18 core biopsy samples are obtained by the radiologist at any given time from each patient. These samples are sent to the pathologist for careful histologic evaluation where standard histologic protocols are followed. Multiple sections from each tissue block containing the core biopsies are routinely performed on all samples.

Radiologists and pathologists play a pivotal role in the diagnostic process by interpreting the results of numerous diagnostic tests. Both imaging and pathology tools are required to properly diagnose, stage or confirm accurate treatment of breast cancer. However, they generally make these interpretations independently and communicate them generally through written reports. This approach can lead to differences in treatment recommendations, creating uncertainty as to the best way to proceed with care and potentially having a negative effect on patient outcomes. Ideally, the pathologist should review the pertinent prebiopsy imaging and specimen radiographs to correlate the morphology of the radiographic target with the histology. Unfortunately, it is common practice to rely on a written description of the targeted lesion provided by the radiologist. Similarly, ideally the radiologist should personally review the tissue slides to assure that the targeted lesion has been properly recognized and diagnosed, and he or she should establish concordance between the histology and imaging and then propose appropriate follow-up care. Regrettably, this is not a common practice and radiologists most often rely on the pathologist's written report.

Radiologists, pathologists, surgeons, and oncologists must interact closely to achieve these common goals. Failure to follow this integrated multidisciplinary approach to breast biopsy specimen review may lead to a misdiagnosis. Ideally, the pathologist should review the pertinent prebiopsy imaging and specimen radiographs to correlate the morphology of the radiographic target with the histology.

Failure to perform proper correlation may result in:
Failure to recognize that the lesion was inadequately sampled
False negative delayed diagnosis of malignancy
Failure to recognize nonmalignant high risk lesions which should prompt additional testing or more aggressive clinical surveillance

BRIEF SUMMARY

The present disclosure relates to a tissue tray for collecting and organizing tissue biopsy samples as they are analyzed and prepared for histological analysis and other analyses. For instance, the tissue tray is adapted for both X-ray and pathologic analyses of breast cancer tissue biopsy samples to facilitate collaboration and diagnosis by radiologists, pathologists, and other medical personnel. In one embodiment, a tissue tray includes an upper surface and a bottom surface, at least one compartment formed in the upper surface of the tray configured to receive tissue and having one or more fluid conduits passing between openings in the upper and bottom surfaces, and at least one marker configured to indicate the orientation of the tray such that the tray is in the same orientation during radiological analysis and pathological analysis.

The tissue tray disclosed herein is engineered to be inserted in routine, commercially available tissue cassettes used by labs for holding and, securing all kinds of tissue specimens for tissue processing. For example, tissue cassettes currently in use can accommodate and securely hold trays having an overall size of about 27 mm×about 25 mm×about 3 mm. One will appreciate, however, that the size of the tissue tray disclosed herein may be modified to fit sample cassettes having different dimensions without departing from the spirit and scope of the present disclosure.

In one embodiment, the tissue tray is designed with four separate compartments with divider walls separating each compartment. In one embodiment, each compartment has dimensions of about 5 mm (width)×about 25 mm (length)×about 2.0 mm (depth). When the lid of the tissue cassette is closed, the lid serves to isolate adjacent compartments from one another, preventing migration or movement of specimens from one compartment to another during transportation or storage.

Each compartment is equipped with a number of holes that are sized and distributed to allow for drainage of the tray during tissue fixation and processing. This design is important for proper tissue fixation and, appropriate tissue processing this prevents the movement or change of orientation of the specimens during drainage.

Each tissue tray has a number of orientation notches or other indicia that indicate the proper orientation and direction when the tissue tray is inserted into a tissue cassette. This orientation notches or other indicia guide the X-ray and histopathological technologists as to the proper orientation of the samples while analyzing X-rays and embedding tissue to mirror the images of the orientation of X-rayed samples. Also the notches may be positioned to allow the outer tissue cassette lid to close freely and securely without interfering with inserted tray.

Cassettes can be fully immersed in solvent, allowing even distribution of solvent over each specimen preventing specimens from degrading or drying.

The tissue tray disclosed herein is superior to devices known in the art. An important concern is the provision of accurate diagnosis for patients screened for conditions such as breast cancer. Patient's safety and welfare is of utmost importance. By utilizing the tissue tray disclosed herein along with the combined pathology/radiology interdisciplinary diagnostic approach, collaboration will be enhanced and patient outcomes will likely be improved.

Using the tissue tray disclosed herein pathologists and radiologist would be able to simultaneously evaluate each core biopsy obtained from each lesions by both histologic and radiologic methods.

The concept is a transformational thought changing the entire health care for the best possible care with no room for error.

Having the correct diagnosis and an agreed upon treatment course would eliminate additional testing, save patient's lives and eliminate delay in diagnosis.

The tissue tray disclosed herein will eliminate tissue damage, loss and lack of appropriate fixation.

The tissue tray disclosed herein will eliminate/reduce mislabeling of specimen that is potentially harmful to patient as samples are already packaged by the radiologist in a sealed container at the patient's bed side.

The tissue tray disclosed herein is radiolucent, making it suitable for all radiologic studies of tissue specimens without the potential problem of hindering the radiologist's ability in reviewing any lesions within the tissues examined.

The tissue tray disclosed herein is suitable for specimen transportation while maintaining the appropriate specimen orientation for pathologic radiologic correlation.

The tissue tray disclosed herein is compatible with all kinds of pathologic procedures. For example, the tissue tray disclosed herein may be designed to withstand formalin, alcohol, xylene and all other types of solvents utilized in a pathology lab for tissue processing. This is useful as the tissue tray disclosed herein is needed to protect tissue during transportation and processing as well is to protect the very expensive tissue processors from by-products of any substance that is mixed with the various solvents during tissue processing.

With slight modifications of compartments sizes and spacing, the tissue tray disclosed herein is applicable for use for other types of small biopsy specimens that require radiologic correlation or certain orientation.

The tissue tray disclosed herein is a new innovative design for handling, transporting and, sorting multi specimens. It is a unique tray system that reduces or eliminates the pitfalls used by old techniques for collecting multi specimens for X-Ray and pathology. The tissue tray disclosed herein ensures that radiological studies can be preformed precisely accurately and methodically.

The tissue tray disclosed herein has the potential of revolutionizing the critically valuable process of combined radiologic and pathologic evaluation of the lesions by radiologists and pathologists.

The tissue tray disclosed herein is made of material that is radiolucent and chemically tolerant. This material allow X-raying of specimen's without interference of image resolution or reduction in image quality of the X-rayed pictures, insuring that radiological studies could be preformed precisely, accurately and methodically.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the invention and are therefore not to be considered limiting of its scope. The embodiments of the invention will be described and explained with additional specificity and detail through the use of the accompanying drawings in which:

In FIG. 7A, tissue core biopsies are haphazardly clumped together eliminating the possibility of identifying which core has what lesion. While samples oriented on the tissue tray in FIG. 7B are oriented in such a way that would help both the radiologist and pathologist in simultaneously evaluating each tissue biopsy core.

DETAILED DESCRIPTION

The present disclosure relates to a tissue tray for collecting and organizing tissue biopsy samples as they are analyzed and prepared for histological analysis and other analyses. For instance, the tissue tray is adapted for both X-ray and pathologic analyses of breast cancer tissue biopsy samples to facilitate collaboration and diagnosis by radiologists, pathologists, and other medical personnel. In one embodiment, a tissue tray includes an upper surface and a bottom surface, at least one compartment formed in the upper surface of the tray configured to receive tissue and having one or more fluid conduits passing between openings in the upper and bottom surfaces, and at least one marker configured to indicate the orientation of the tray such that the tray is in the same orientation during radiological analysis and pathological analysis.

In one embodiment, a tissue tray is disclosed. The tissue tray includes a tray having a material conducive to both radiological analysis and to pathological analysis, the tray comprising an upper surface and a bottom surface, at least one compartment formed in the upper surface of the tray configured to receive tissue and having one or more fluid conduits passing between openings in the upper and bottom surfaces; and at least one marker configured to indicate the orientation of the tray such that the tray is in the same orientation during radiological analysis and pathological analysis.

Figure 1:
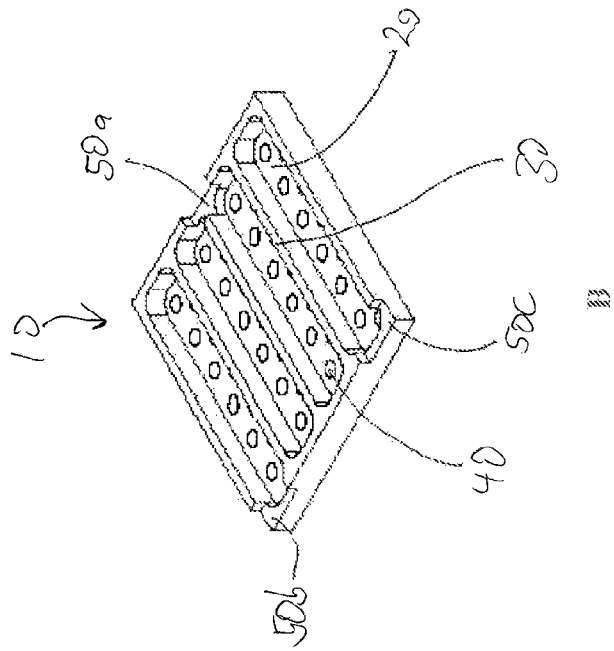
FIGS. 1A-1C illustrate several views of a tissue tray, according to one embodiment of the present invention.
Figure 1:
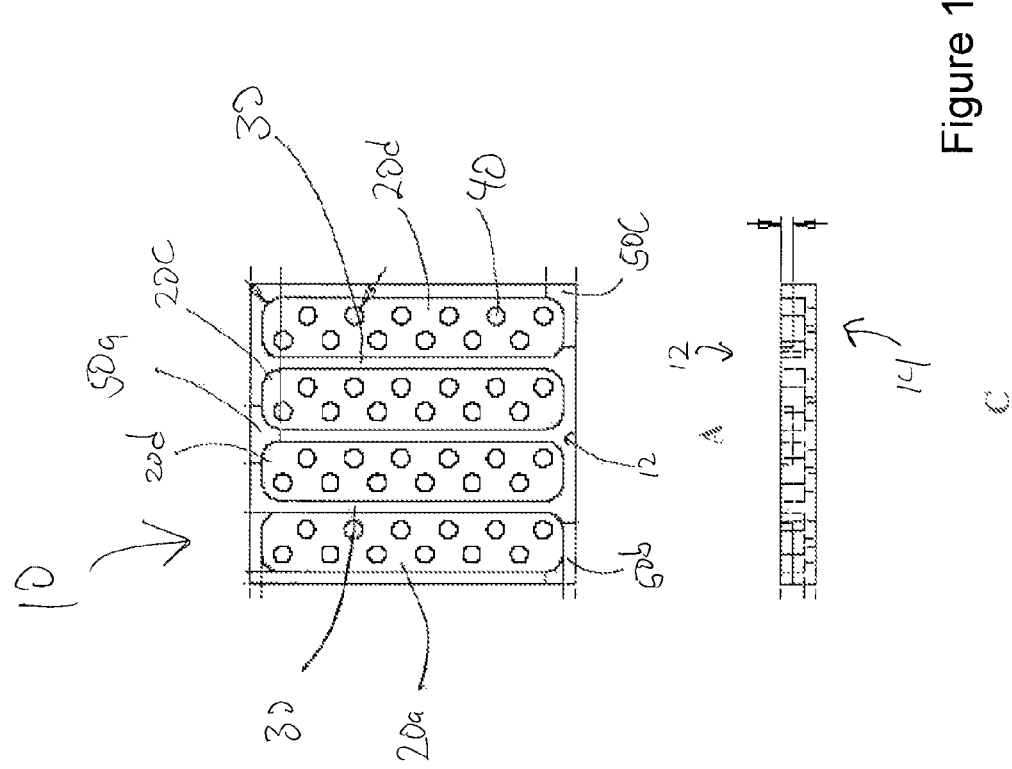
Figure 2:
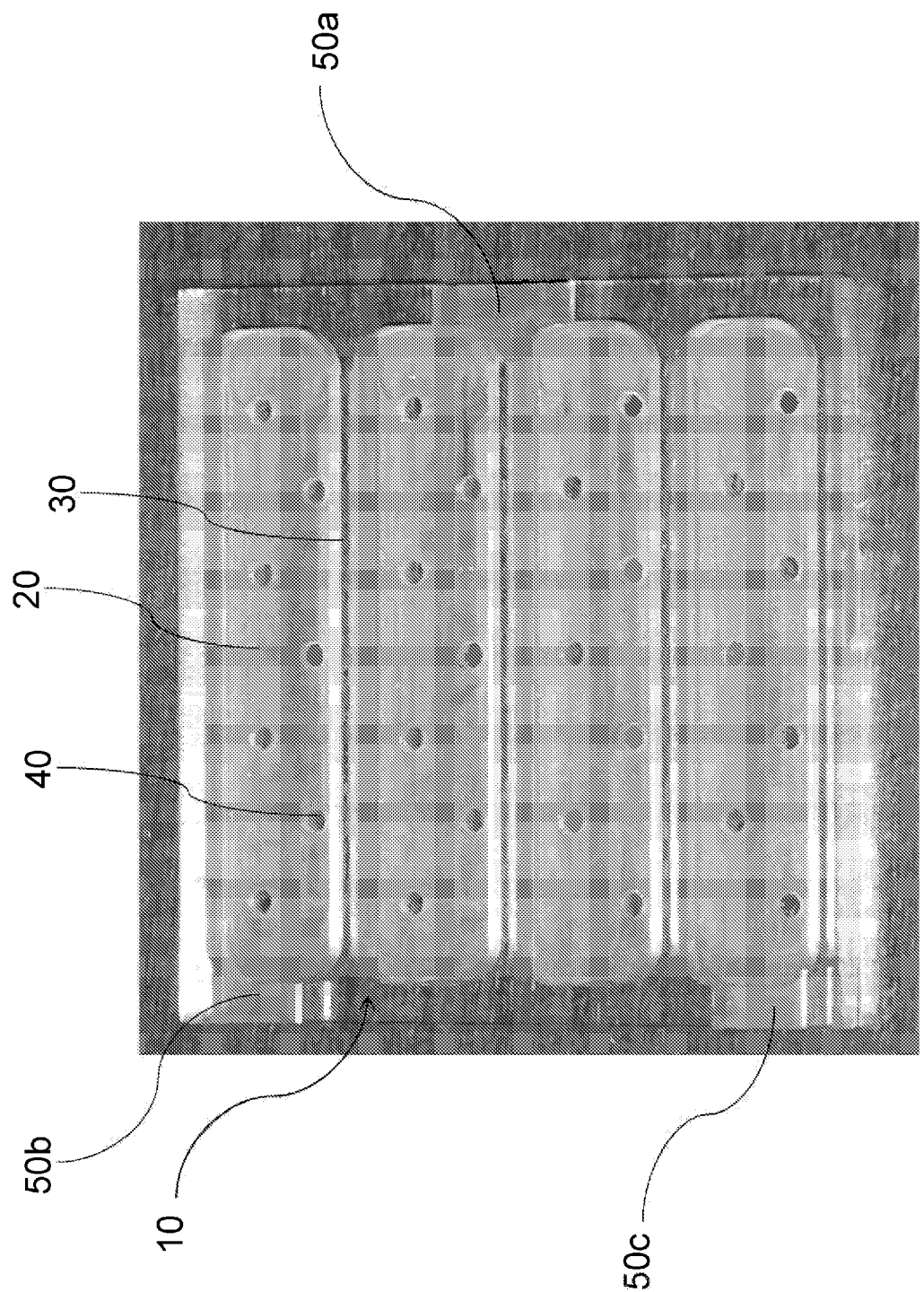
FIG. 2 illustrates a top view of a tissue tray, according to one embodiment of the present invention.
Figure 3:
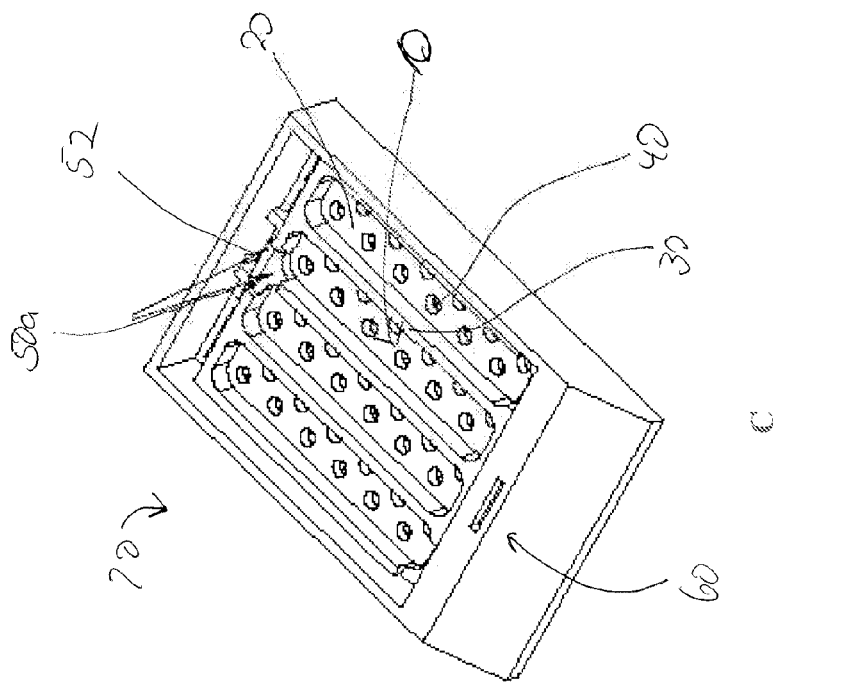
FIGS. 3A-3D illustrate several views of a tissue tray and an associated tissue cassette, according to one embodiment of the present invention.
Figure 3:
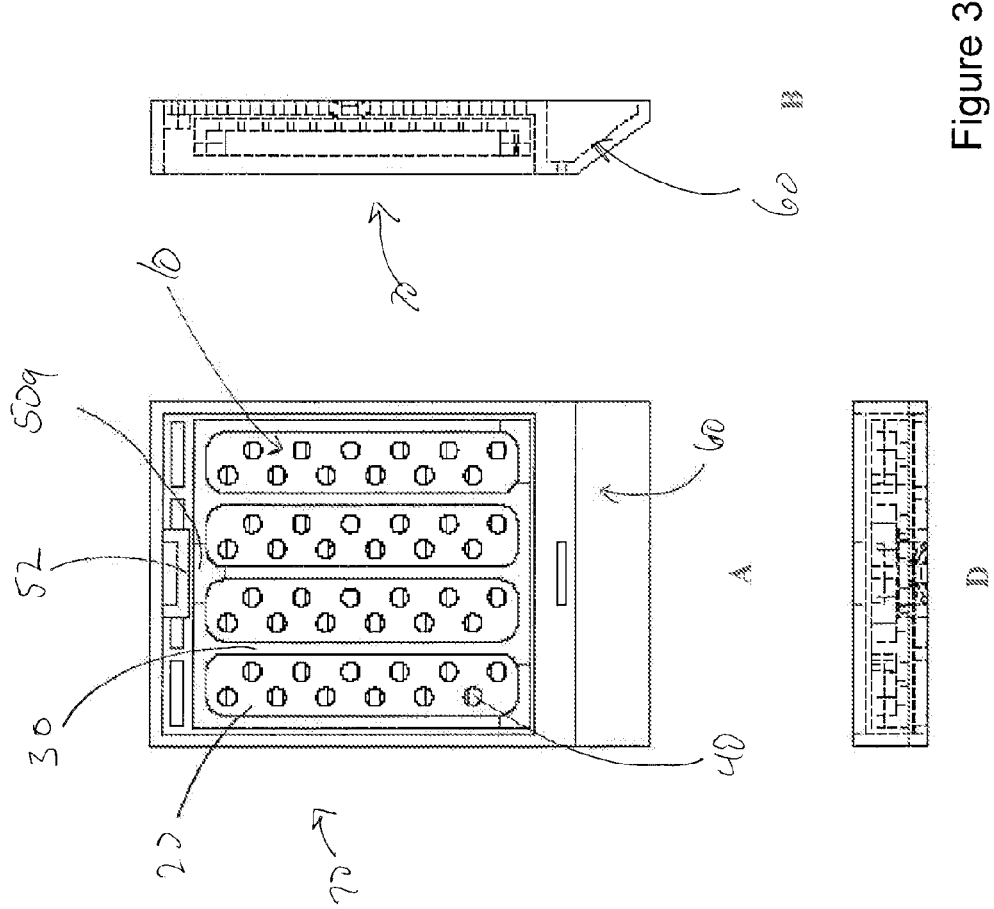

Referring now to FIGS. 1A-1C, several views of a tissue tray 10 are illustrated, according to one embodiment of the present invention. An alternate view of the tissue tray 10 is illustrated in FIG. 2. The tissue tray 10 includes an upper surface 12 and a bottom surface 14. Formed in the upper surface 12 are a number of tissue compartments that are configured to hold tissue biopsy samples. In the illustrated embodiment, the tissue tray 10 includes four tissue compartments 20a-20d. In one embodiment, each compartment has dimensions of about 5 mm (width)×about 25 mm (length)×about 2.0 mm (depth). One will appreciate, however, that other embodiments may include more or fewer tissue compartments.

In one embodiment, the length of the tray 10 is between about 20 millimeters to about 40 millimeters and the width of the tray 10 is between about 20 millimeters to about 40 millimeters. In one embodiment, the depth of the tray 10 is between about 2 millimeters to about 5 millimeters.

Each of the four tissue compartments 20a-20d are separated by divider walls 30. In one embodiment, each divider wall 20 is between about 0.5 millimeters and about 2 millimeters thick. Formed in each of the four tissue compartments 20a-20d are a number of fluid conduits 40 passing between openings in the upper 12 and bottom 14 surfaces. The fluid conduits 40 are positioned and sized to allow fluid (e.g., bodily fluids or fixing fluids) to drain from the tissue samples after the tissue samples are removed from the patient's body and placed in the sample tray 10. Likewise, the fluid conduits 40 are positioned and sized such that the tissue samples cannot fall out of the tray 10. In one embodiment, the fluid conduits 40 have a size ranging from about 1 mm to about 2 mm, or about 1.5 mm. In the illustrated embodiment, the fluid conduits 40 are generally circular holes. One will appreciate, however, that other shapes can be used so long as the fluid conduits 40 are sized and positioned to allow fluid to drain from the tissue samples while simultaneously preventing the tissue from falling out of the tray 10.

In one embodiment, the at least one compartment (e.g., 20a) is an elongate compartment having a length between about 20 millimeters and about 40 millimeters, a width between about 2 millimeters and about 10 millimeters, and a depth between about 1 millimeter and about 4 millimeters. In one embodiment, each compartment of the plurality of compartments is substantially the same size. In one embodiment, the elongate compartments of the plurality of compartments are configured in a parallel arrangement.

The tissue tray 10 further includes a number of includes a number of orientation markers 50a-50c. In the illustrated embodiment, the orientation markers 50a-50c are notches formed in the upper surface 12 of the tissue tray. In other embodiments, different indicia such as numbers, hash marks, and the like may be used. Additionally, the orientation markers may be equipped with a radiopaque material (e.g., tungsten or a tungsten-filled thermoplastic) to facilitate orientation of the tissue tray in X-ray photographs.

Figure 4:
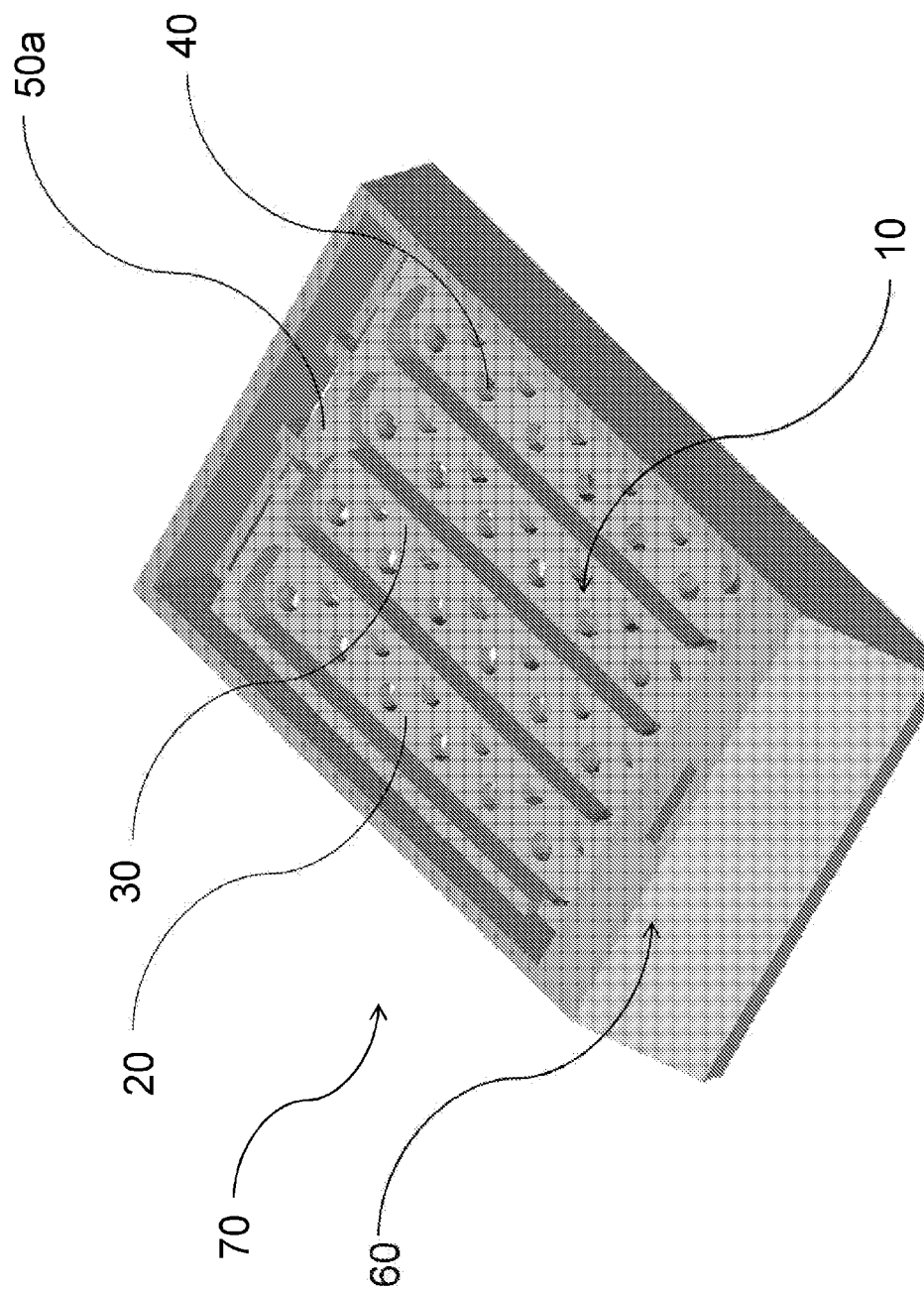
FIG. 4 illustrates a view of a tissue tray and an associated tissue cassette, according to one embodiment of the present invention.
Figure 5:
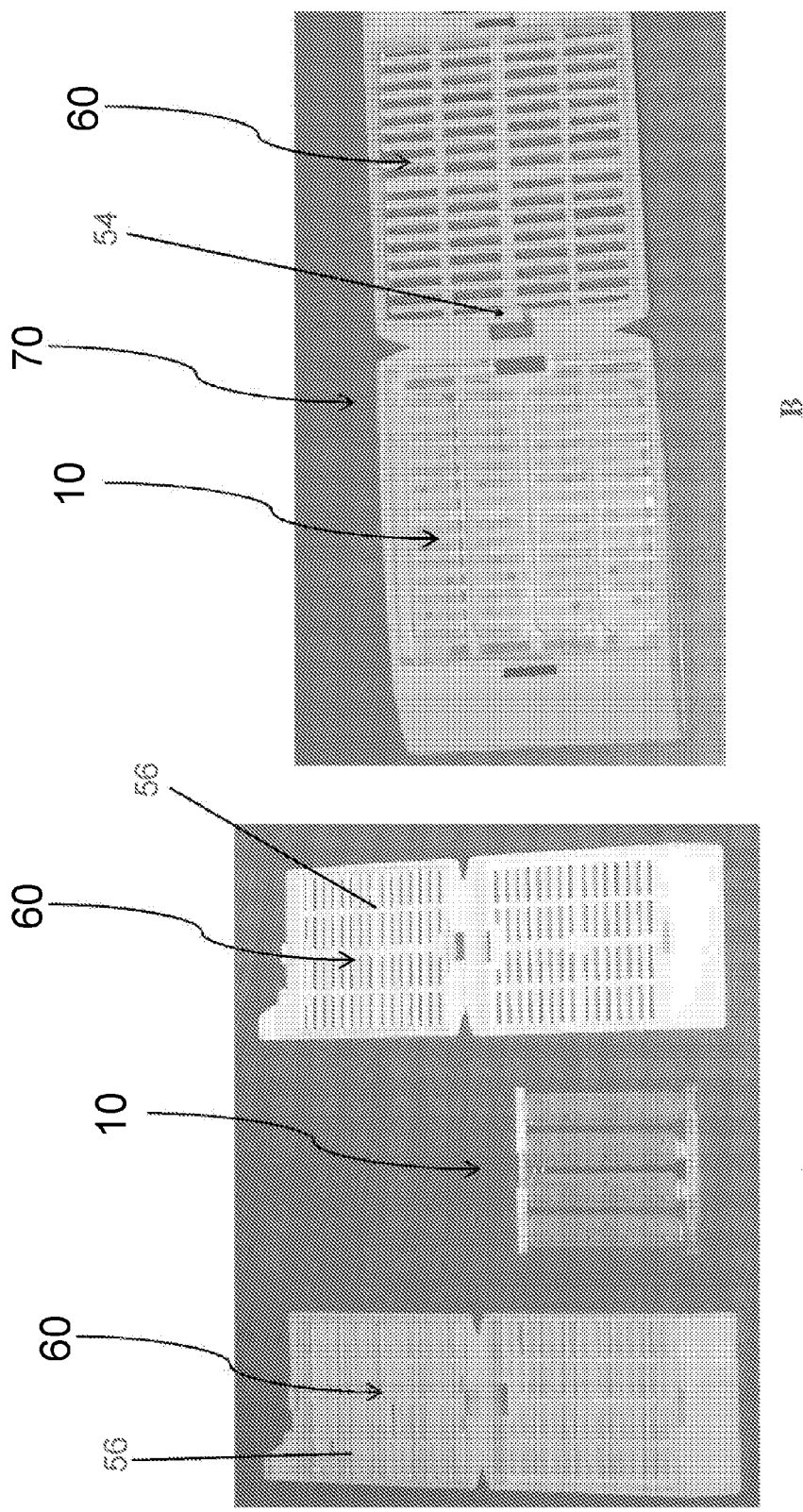
FIGS. 5A-5B illustrate several views of a tissue tray and an associated tissue cassette, according to one embodiment of the present invention.

In one embodiment, the tissue tray 10 is configured to be received in a tissue cassette 60. FIGS. 3A-3D illustrate several views of the tissue tray 10 and an associated tissue cassette 60. The assembly of the tissue tray 10 and the associated tissue cassette 60 is labeled at 70. FIGS. 4-5B illustrate alternative views of the tissue tray 10 and the associated tissue cassette 60. The tissue cassette 60 is a tissue holder routinely used by labs for holding and, securing all kinds of tissue specimens for tissue processing. For example, tissue cassettes 60 currently in use can accommodate and securely hold trays 10 having an overall size of about 27 mm×about 25 mm×about 3 mm. One will appreciate, however, that the size of the tissue tray 10 disclosed herein may be modified to fit sample cassettes 60 having different dimensions without departing from the spirit and scope of the present disclosure.

In the illustrated, orientation notch 50a is positioned to accept tab 52 in the tissue cassette 60. Positioning tab 52 in notch 50a further ensures that the tissue tray 10 is correctly oriented in the tissue cassette 60 and facilitates identification and tracking of particular tissue biopsy samples. Referring now to FIGS. 5A and 5B a second tab 54 is shown on the lid 56 of the tissue cassette 60. The orientation tab 50a is positioned to accommodate the second tab 54 to allow the lid 56 to close. As with tab 52, this ensures that the tissue tray 10 is correctly oriented in the tissue cassette 60 and facilitates identification and tracking of particular tissue biopsy samples.

When the lid 56 of the tissue cassette 60 is closed, the lid serves 56 to isolate adjacent compartments 20 of the tissue tray 10 from one another, preventing migration or movement of specimens from one compartment to another during transportation or storage.

In one embodiment, the material used to fabricate the tray 10 is transparent and radiolucent material. In one embodiment, the tissue tray 10 may be fabricated from the group consisting of glass, poly(methyl methacrylate), Plexiglas™, polycarbonates, polyethylenes, polypropylenes, and the like. In one embodiment, plastic materials such as Plexiglas™ are preferred due to their radiolucent nature and their solvent resistance. In one embodiment, the material used to fabricate the tray 10 is stable with solvents such as, but not limited to, formalin, alcohols, xylene, and other solvents commonly used for tissue fixing in a pathology lab.

In one embodiment, one or more of the compartments (e.g., compartment 20a) may be subdivided into a plurality of compartments formed in the upper surface of the tray configured to receive tissue. In one embodiment, the plurality of compartments are separated by one or more divider walls. In one embodiment, the each compartment of the plurality of compartments includes a plurality of fluid conduits. In one embodiment, each compartment of the plurality of compartments includes a plurality of conduits arraigned in a pattern to provide the at least one marker. In one embodiment, at least one compartment of the plurality of compartments includes a plurality of conduits arraigned in a pattern to provide the at least one marker.

In one embodiment, the one or more fluid conduits of the at least four compartments (20a-20d) are distributed in a uniform pattern.

A tissue tray according to claim 1, wherein the at least one marker (e.g., 50a) comprises a notch in the upper surface of the tray. In one embodiment, the at least one marker is constructed of a material having different radiolucent properties than the material of the tray. In one embodiment, the at least one marker is a visually distinguishable color from a color of the tray material. In one embodiment, the at least one marker comprises a plurality of markers configured to indicate the orientation of the tray. In one embodiment, the plurality of makers comprises at least two notches in the upper surface of the tray.

In yet another embodiment, a tissue tray is disclosed. The tissue tray includes a tray constructed of a transparent and radiolucent material that is stable to formalin, alcohol, and xylene, wherein the length of the tray is between about 20 millimeters to about 40 millimeters, wherein the width of the tray is between about 20 millimeters to about 40 millimeters, and wherein the depth, which is measured between an upper surface and a lower surface of the tray, is between about 2 millimeters to about 5 millimeters. The tray includes at least four elongate compartments formed in the upper surface of the tray configured to receive tissue, wherein each elongate compartment has a length between about 20 millimeters and about 40 millimeters, a width between about 2 millimeters and about 10 millimeters, and a depth between about 1 millimeter and about 4 millimeters, and wherein the elongate compartments are configured in a parallel configuration in the upper surface of the tray, each of the at least four compartments being separated by a divider wall that is between about 0.5 milllimeters and about 1.5 millimeters. Each of the at least four elongate compartments comprises a bottom surface having formed therein a plurality of holes that extend through the bottom surface of the tray, wherein the each of the holes is between about 0.5 and about 1.5 millimeters in diameter. The tray includes at least two notches in the upper surface of the tray configured to indicate the orientation of the tray.

In still yet another embodiment, a tissue tray system is disclosed. The tissue tray system includes at least one tissue cassette comprising a container and a lid, wherein the tissue cassette is configured to receive at least one tissue tray when the lid is in an open configuration, and wherein the tissue cassette encloses the at least one tissue tray when the lid is in a closed configuration. The at least one tissue tray comprising an upper surface, a bottom surface, at least one compartment formed in the upper surface of the at least one tissue tray configured to receive tissue, and at least one marker configured to indicate the orientation of the at least one tray.

In still yet another embodiment, a method of making a tissue tray is disclosed. The method of making the tray includes (1) selecting a transparent and radiolucent material that is stable to formalin, alcohol, and xylene, (2) providing a tissue tray mold, the mold configured to provide a molded tissue tray comprising an upper surface and a bottom surface, at least one compartment formed in the upper surface of the tissue tray configured to receive tissue; and at least one marker configured to indicate the orientation of the tissue tray, and (3) casting the transparent and radiolucent material in the tissue tray mold.

In one embodiment, the method of casting the radiolucent material in the tissue tray mold is selected from the group consisting of injection molding, compression molding, blow molding, and thermoforming.

In still yet another embodiment, a method of making a tissue tray is disclosed. The method includes (1) selecting a transparent and radiolucent material that is stable to formalin, alcohol, and xylene, (2) providing a tissue-tray-sized member of the transparent and radiolucent material having an upper surface and a bottom surface, (3) forming at least one compartment in the upper surface of the tissue-tray-sized member configured to receive tissue, and (4) forming at least one marker in the tissue-tray-sized member configured to indicate the orientation of the tissue tray.

In still yet another embodiment, a method of using a tissue tray is disclosed. The method includes (1) providing a tissue tray comprising an upper surface and a bottom surface, at least one compartment formed in the upper surface of the tissue tray configured to receive tissue, and at least one marker configured to indicate the orientation of the tissue tray, wherein the tissue tray includes a transparent and a radiolucent material that is stable with formalin, alcohol, and xylene, (2) providing at least one tissue biopsy, (3) placing the at least one tissue biopsy in the at least one compartment of the tissue tray, (4) orienting the tissue tray using the at least one marker of the tissue tray, and (5) performing at least one radiological operation on the at least one tissue biopsy in the at least one compartment of the tissue tray.

In one embodiment, the method of using the tissue tray further includes fixing the at least one tissue biopsy in the at least one compartment of the tissue tray in formalin.

In one embodiment, the method of using the tissue tray further includes (1) placing the tissue tray containing the at least one tissue biopsy in a tissue cassette and (2) performing at least one pathological operation on the at least one tissue biopsy.

In one embodiment, the method of using the tissue tray further includes (1) using the at least one marker of the tissue tray to correlate results of the at least one radiological test and the at least one pathological operation. In one embodiment, the at least one radiological test comprises an X-ray.

In still yet another embodiment, a method of using a tissue tray is disclosed. The method includes (1) disposing at least one tissue biopsy sample in a tissue tray, the tissue tray comprising an upper surface and a bottom surface, at least one compartment formed in the upper surface of the tissue tray configured to receive the at least one tissue biopsy sample, and at least one marker configured to indicate the orientation of the tissue tray, wherein the tissue tray includes a transparent and a radiolucent material, (2) orienting the tissue tray using the at least one marker of the tissue tray, and (3) screening the at least one tissue biopsy sample for an abnomality.

In one embodiment, the screening includes at least one of an X-ray examination or a histological examination. In one embodiment, the abnormality may include a cancerous lesion or a microcalcification.

In one embodiment, the method further includes (1) scanning a result of at least one of the X-ray examination or the histological examination into a computer readable format, (2) sharing the computer readable format of the result of least one of the X-ray examination or the histological examination over a computer network, and (3) making a collaborative analysis of the at least one of the X-ray examination or the histological examination among recipients of the computer readable format. In one embodiment, the method can further include requesting at least one addition view of the at least one of the X-ray examination or the histological examination based on the collaborative analysis.

In one embodiment, the screening includes fixing the at least one tissue biopsy in the at least one compartment of the tissue tray in formalin.

In one embodiment, the method further includes (1) placing the tissue tray containing the at least one tissue biopsy in the a tissue cassette, and (2) performing at least one pathological operation on the at least one tissue biopsy.

In one embodiment, the method further includes (1) using the at least one marker of the tissue tray to correlate results of at least one radiological test and at least one pathological operation.

Investigators have quickly realized the importance of a multidisciplinary approach with the collaboration of radiologist, pathologists and surgeons for accurate histopathologic diagnosis and to insure the success of any Core Needle Biopsy ("CNB") program. The tissue trays and methods described herein can be integral to developing systematic approaches to collecting and tracking samples. Likewise, the tissue trays and methods described herein can be integral to developing collaborative approaches to analysis of samples (e.g., X-ray and histologic analysis) and diagnosis and treatment of patients.

In a pioneering effort at the University of Kansas Medical center, radiologists and pathologists (Dr. Tawfik one of the inventors) understood the tremendous value of collaborating together to improve diagnostic concordance. They reached across the traditional silos that separate the daily practice of radiology from the daily practice of pathology. They are currently working side by side to review each other's primary images and slides and issue an integrated diagnostic report for breast cancer patients. In a very innovative way pathologists and radiologist at the University of Kansas Medical Center understood the values of communication in their practice. They overcame measure hurdle such as manpower, time and geographic constrains that could make interdisciplinary communication difficult. They currently meet weekly via audio-videoconference to view pathology findings and radiologic images simultaneously and thoroughly consider treatment recommendations for patients screened for breast cancer. In their meetings the different specialists discuss their findings and resolve any differences between radiology images and pathology reports to create a consistent treatment plan for each patient.

A pilot study of 122 biopsies obtained from 106 patients found that this interdisciplinary approach altered/impacted treatment plan decisions in over one-third of cases. The majority of these issues were related to identification of microcalcifications by the pathologist and its correlation with radiologic findings.

Improvements in breast cancer screening as well as a shift from open surgical to percutaneous image guided biopsies have resulted in significant decrease in size of suspicious lesions detected on imaging studies. Currently, sample sizes range from 2-3 millimeters in diameter and 10-20 millimeters in length and the majority of targeted lesions range from 5-15 millimeters in diameter. Therefore histologic evaluation of the core specimens must be performed at step levels to adequately screen the tissue samples. At least 3-6 levels are generally required to screen a 3-mm in diameter core.

The reduction in detected lesion size is best exemplified by the detection of small clusters of calcifications (called microcalcifications) suspicious for certain types of breast cancer type called "ductal carcinoma in situ." Furthermore, the target lesions are usually surrounded by breast tissue that may be normal or may represent one of the many benign pathologies that often coexist with the targeted lesion; if the target lesion is not clearly recognized, a diagnosis maybe incorrectly rendered based on the surrounding tissue. Taken together, these factors create new challenges for pathologists, who are now required to identify lesions such as microcalcifications within the specimen. As a result, a pathologist might not view the tissue in the same way as the radiologist, necessitating closer communication between radiologists and pathologists for accurate diagnoses. Furthermore, since pathologists do not see patients directly, they may not have full information about a case. Discordance between radiologic and pathologic findings may lead to false negative results, causing delayed diagnosis of malignancy. Discordance can also result in the failure to recognize pre-malignant lesions that require further testing and/or careful monitoring.

There are currently no standardized protocols for the assessment of mammographically detected calcifications. Minute foci of microcalcifications are usually reported as rare calcifications identified giving the false impression that those foci are the ones that are noted by the radiologist during mammographic evaluation. Some of these cases are actually below the radiologic resolution capability of the mammogram and could represent areas unrelated to the primary lesion of concern.

There is a general agreement between radiologists and pathologists, that before considering specimens to be definitively devoid of calcification, tissue blocks are subjected to aggressive deeper sectioning and eventually radiography for documentation of the lack of calcification. It is agreed upon that in this group of patients lesions are then considered to be missed by the radiologist and are usually subjected to further evaluations including repeat CNBs or open biopsies for evaluation of their mammographic abnormalities.

Very few studies have attempted to address the issue of mammographic-histologic correlation of microcalcifications in CNB of the breast. Bagnall et al., have studied sampling adequacy, optimum number of core biopsies containing calcification, and number of calcium flecks and their relationship to CNBs' sensitivity in accurately diagnosing non-palpable lesions. They have shown that number of flecks of calcium and number of cores with calcification was critical for improving diagnostic sensitivity. Five or more flecks of calcium and 3 or more cores with calcification were associated with a 100% absolute sensitivity for malignancy.

Dahlstrom et al., have found a poor correlation between radiology and histology with respect to the appearance and distribution of calcification in CNBs. They have also found that microcalcifications size was a valuable indicator that the mammographically suspicious lesions were examined histologically. Any microcalcification size of <100 μm may not be significant as it was below the limit of radiologic sensitivity of calcifications and may not represent the calcification seen mammographically. In a subsequent study, the same group further assessed the value of specimen radiography of core biopsies and the usefulness of measuring size of microcalcifications on tissue sections and their relationship to diagnostic outcome. They advocate specimen radiography and the demonstration of microcalcifications of >100 μm were critical assessment of "suspicious" calcification.

Reasons for a discrepancy between mammographically detected calcification and tissue sections devoid of microcalcifications are several. A primary reason is the inadequate number of sections cut from the tissue block. In such cases, tissue block radiography is essential for documentation of the presence or absence of calcification. Tissue blocks with microcalcifications are subjected to deeper sectioning and are microscopically examined until the area with microcalcifications appears in the sections.

In a previous study by one of the inventors (Dr Tawfik and his group) they attempted to standardize the procedure of CNB program in correlating histologic findings including microcalcifications size with mammographically detectable calcification. They recommended a systematic approach to standardize reporting of microcalcifications in CNBs. They stressed that pathologists should routinely report the size of microcalcifications in their reports and correlate their findings with the tissue block radiologic findings. Discrepant "false-positive with <100 μm microcalcifications" biopsies should be considered non-diagnostic and should be handled clinically the same way as "negative" biopsies. In that study they were able to resolve discrepancy in 12 out of 16 samples.

The present invention is in the field of trays for tissue biopsy samples that facilitate tissue examination and analysis by radiologists and pathologists. It is particularly in the field of obtaining, orienting, handling tissue core biopsies for later processing and examination by pathologists. While the different radiologic tools are useful in localizing a tumor, a suspicious diagnosis, or an area of microcalcifications, the nature of that lesion can only be determined by a pathologist's examination. Current radiologic devices collect samples that do not allow or provide a method to separate different core biopsies from each other. Therefore, there is a need for an apparatus or a method to handle specimens for efficiently separating them from each other in an appropriate fashion that will enable the pathologists and radiologists to simultaneous analysis and correlate results with each other.

Currently, once a tissue samples are harvested by the radiologists from a suspicious lesion, they are transported to the pathology lab for processing in formalin containers labeled with the patient's name and the location of the lesion along with a pathology requisition. Usually multiple numbers of core biopsies are obtained from each lesion varying from 2-15 biopsies per lesion or sometimes more. According to current practice, these biopsies are pooled together in one container.

Once in the pathology lab, the specimen is logged into the manual or computerized anatomic pathology system and is assigned a unique surgical pathology accession number. This number is placed on the specimen container and is subsequently used to label cassettes, histology slides and the final surgical pathology report. The specimen is logged into the pathology system, and then is physically described by a pathologist or his/her assistant. This is the description portion of the process known as "grossing-in" the specimen. Pathologists and/or their assistants start handling those biopsies and randomly transfer them into tissue cassettes for processing before making histologic sections for microscopic evaluation.

The first problem with the prior art: With no way to control where the sample lodges in the container, the sample may stick to the lid or sides of the container and become dried out before it reaches the pathology lab; rendering it difficult, if not impossible to interpret. In addition, the samples may be extremely small and may be hard to locate and retrieve from the container. Therefore there is a need for a device that would maintain the cores completely immersed into formalin for adequate fixation Second problem of the prior art: There is lack of any device that is acceptable for adequate specimen X-ray in an away that is practical and efficient. Although there are ways to X-ray specimens after their removal from patients, those specimens are then collected in a random fashion and pooled together in a way that impedes the process of pathologic/ radiologic correlation in the diagnosis. Therefore, there is a need for a device that facilitates the process of X-raying tissue specimens in a practical and efficient way.

Third problem of the prior art: The inability for the pathologist to either identify and/or localize suspicious abnormalities such as microcalcifications within individual tissue cores. That is, some or all cores may have microcalcifications and other lesions of interest; using current best practices, it is difficult if not impossible to correlate X-ray data to individual tissue cores for histologic analysis. For example, when tissue biopsy samples are collected they are typically placed in a single container. When these samples are X-rayed, even if evidence of microcalcifications or other lesions of interest is detected, once the specimens are transported to the pathology lab there is no way to identify which core has what type of microcalcifications.

Figure 6:
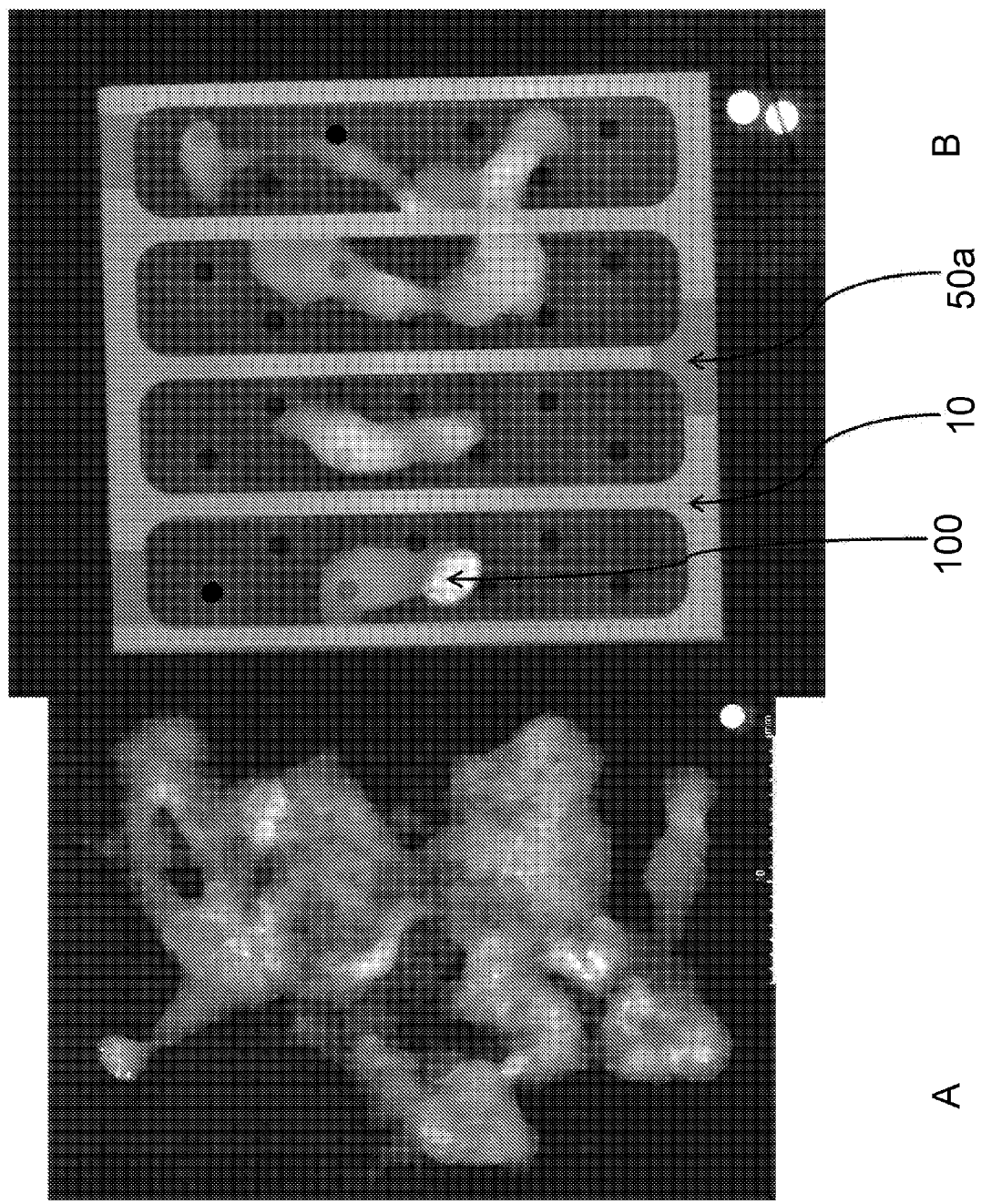
FIGS. 6A-6B illustrate comparative pictures of X-rayed breast tissue biopsies.

This is highlighted in FIG. 6A-6B. FIG. 6B illustrates an X-ray of tissue biopsy samples jumbled together in a single jar. There is clear evidence of microcalcifications and other lesions of interest, but since the samples are jumbled together in a single jar there is no way to correlate individual lesions to individual samples.

In contrast, the tissue trays and methods described herein makes it possible to provide the ability to maintain critical localization and/or tissue orientation throughout these steps and eliminate human errors in the associated manual steps and procedures. That is, the tissue trays and methods described herein can be used to maintain the localization and orientation of the tissue sample from the time of obtained the tissue samples from the patient, gross-in throughout grossing the specimen and the tissue processing procedure and continuing through the wax embedding stage until slides are prepared for pathologic evaluation.

The first step of analysis is illustrated in FIG. 6B. FIG. 6B illustrates an X-ray of a tissue tray 10 that contains a number is biopsy tissue sample (e.g., sample 100). Orientation notch 50a is labeled for reference. As can be seen in contrast to FIG. 6A, the samples are clearly oriented such that lesions in individual samples can be identified (e.g., the bright region of sample 100) and monitored through the tissue processing procedure and continuing through the wax embedding stage until slides are prepared for pathologic evaluation.

Tissue core biopsy samples oriented one by one in their respective location by the radiologist in the tissue trays are X-rayed to localize and identify the different lesions in the different cores as well as localize the lesion(s) within each core. X-ray studies are recorded by the radiologist for future correlative studies by them with the pathologist. Following X-ray studies the different tissue trays labeled and numbered are put formalin containers as usual and sent to the pathology lab as usual.

Once received in the pathology lab, formalin containers are routinely handled by the pathologists and their assistants as usual. Tissue trays are transferred into other tissue cassettes with computerized labeling as per each lab's standard procedures. All cassettes are later put into a tissue processor by the end of the days following adequate fixation, where the tissue is subjected to a sequence of solutions and heat. These solutions gradually replace water in the cells with alcohol, followed by xylene, and ultimately by wax. That allows the wax-impregnated tissue a similar consistency to the wax surrounding the tissue in the next step. Following the completion of tissue processing at the embedding station, a histotechnologist removes the specimens from the cassettes for embedding into tissue blocks.

Figure 7:
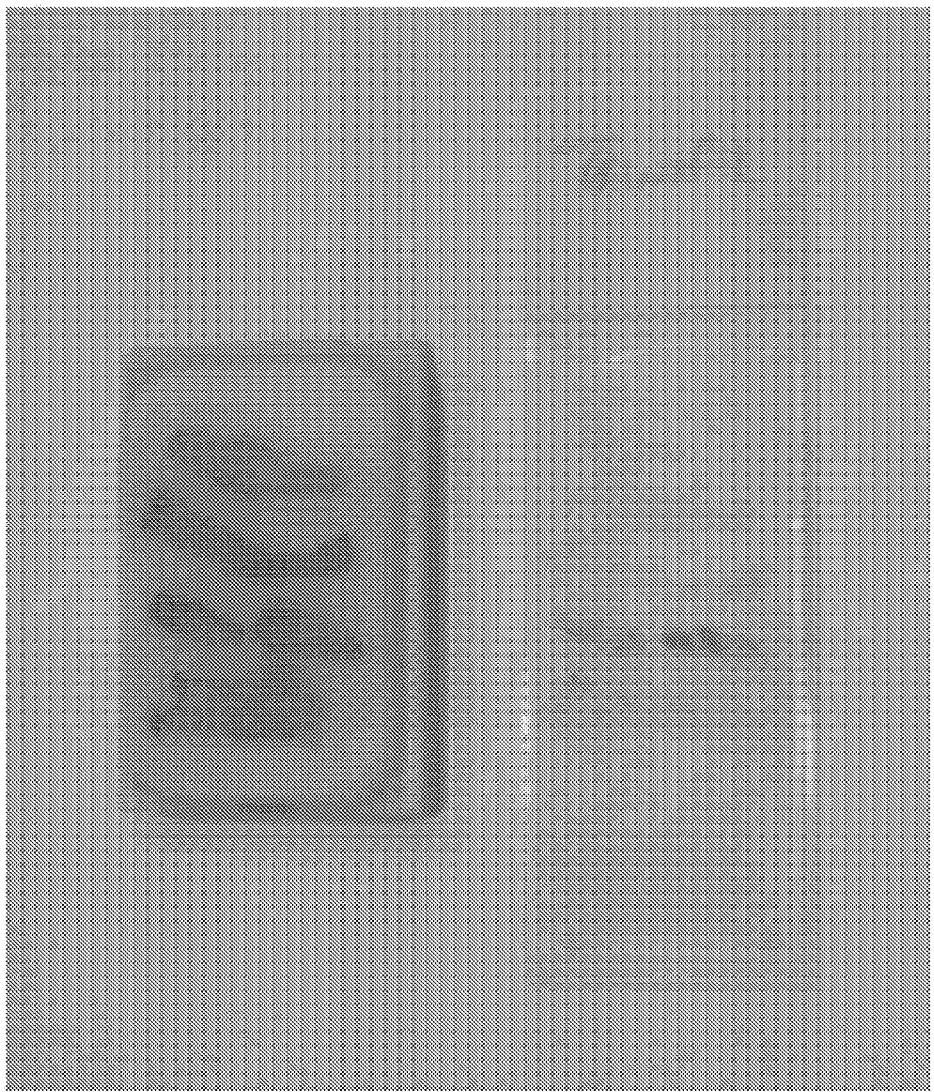
FIG. 7 illustrates a representative sample of breast biopsy handled, processed, embedded in cassettes and sectioned and stained for histologic evaluation by a pathologist.

As illustrated in FIG. 7, each core of tissue is placed and oriented into a mold in the same sequence of orientation into the tissue trays. An embedding medium such as hot (molten) paraffin wax is poured into the mold to immobilize the tissue in a solid block of wax. After cooling, the wax block is removed from the mold, placed into a microtome and sectioned into thin slices approximately 4-6 microns thick. These sections are floated onto glass slides, stained, cover-slipped, and are then ready for microscopic examination.

Figure 8:
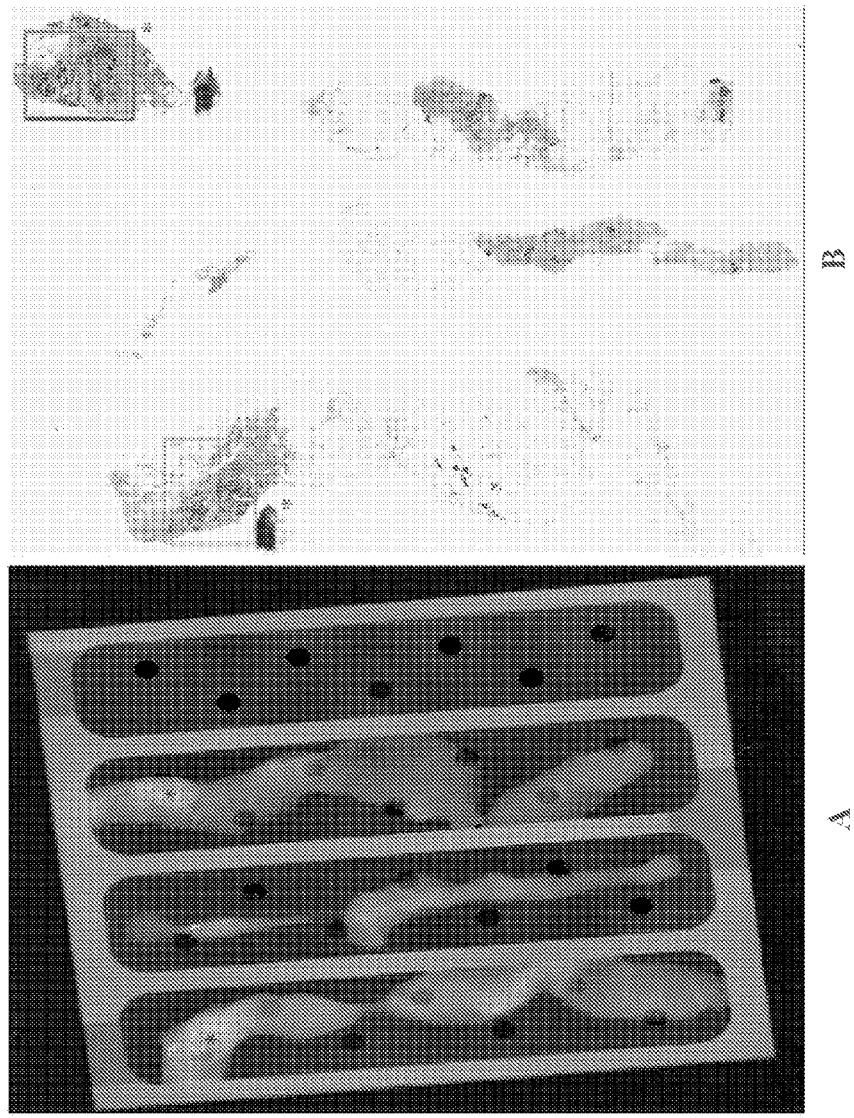
FIG. 8 illustrates a side-by-side comparison between X-ray and histologic analyses of tissue biopsies showing similarity of size, shape and localization of the different lesions in both radiologic and histologic images.

Finally, referring to FIGS. 8A-8B, a composite photograph highlights the value of the tissue tray and the associated methods of using the tissue tray described herein. Tissue core biopsies are put into tissue trays and are X-rayed as shown on FIG. 8A. Tissue sections from the same sample as shown in Figure B. Lesions identified in X-ray analysis in FIG. 8A (shown at the asterisks) are also clearly identifiable in FIG. 8B at the asterisks. That is, one can readily appreciate the similarity of size, shape and localization of the different lesions in both radiologic and histologic images.

1. The newly proposed device is superior to the prior art. Our primary concern is the provision of accurate diagnosis for patient screened for breast cancer. Patient's safety and welfare is of utmost importance. By utilizing the tissue tray disclosed herein along with the combined pathology radiology interdisciplinary diagnostic approach the guessing game will be completely eliminated from the diagnosis.

2. Pathologists and radiologist would be able to simultaneously evaluate each and every core biopsy obtained from each lesion by both histologic and radiologic methods.

3. The concept is a transformational thought changing the entire health care for the best possible care with no room for error.

4. Having the correct un-doubtful results from the first time would eliminate additional testing, save patient's lives and eliminate delay in diagnosis.

5. This technology will eliminate tissue damage, loss and lack of appropriate fixation.

6. This technology will eliminate/reduce mislabeling of specimen that is potentially harmful to patient as samples are already packaged by the radiologist in a sealed container at the patient's bed side.

7. This device is radiolucent, making it suitable for all radiologic studies of tissue specimens without the potential problem of hindering the radiologist's ability in reviewing any lesions within the tissues examined.

8. This device is suitable for specimen transportation while maintaining the appropriate specimen orientation for pathologic radiologic correlation.

9. This device is suitable for all kinds of pathologic procedures. It withstands formalin, alcohol, xylene and all other types of solvents utilized in a pathology lab for tissue processing. This is of critical importance as such a device is needed to protect tissue during transportation and processing as well is to protect the very expensive tissue processors from by-products of any substance that is mixed with the various solvents during tissue processing.

10. With slight modifications of compartments sizes and spacing, the device is applicable for use for other types of small biopsy specimens that require radiologic correlation or certain orientation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tissue tray comprising:
   a tray having a material conducive to both radiological analysis and to pathological analysis, the tray comprising an upper surface and a bottom surface, wherein the tray material is a transparent and radiolucent material;
   at least one compartment formed in the upper surface of the tray and recessed toward the bottom surface of the tray, the at least one compartment configured to receive tissue and having one or more fluid conduits passing between openings in the upper and bottom surfaces; and
   at least one marker configured to indicate an orientation of the tray such that the tray is in the same orientation during radiological analysis and pathological analysis, wherein the at least one marker includes an orientation notch and wherein the at least one marker is located on the tray in a fixed location relative to the tray, and wherein the tray is configured to preserve orientation of tissue placed therein for correlation of radiologic analysis, tissue fixing, and histo-pathological examination.

2. A tissue tray according to claim 1, wherein the tray is configured to be received in a tissue cassette.

3. A tissue tray according to claim 1, wherein tray material is stable with formalin.

4. A tissue tray according to claim 1, wherein the tray material is stable with alcohol.

5. A tissue tray according to claim 1, wherein the tray material is stable with xylene.

6. A tissue tray according to claim 1, wherein the tray material is stable with pathological solvents.

7. A tissue tray according to claim 1, wherein the at least one compartment includes a plurality of compartments formed in the upper surface of the tray configured to receive tissue.

8. A tissue tray according to claim 7, wherein the plurality of compartments are separated by one or more divider walls.

9. A tissue tray according to claim 1, wherein the at least one compartment includes at least four compartments formed in the upper surface of the tray configured to receive tissue.

10. A tissue tray according to claim 9, wherein the one or more fluid conduits of the at least four compartments are distributed in a uniform pattern.

11. A tissue tray according to claim 1, wherein the at least one compartment includes a plurality of conduits.

12. A tissue tray according to claim 1, wherein the at least one compartment includes a plurality of conduits arranged in a pattern to provide the at least one marker.

13. A tissue tray according to claim 1, wherein the at least one compartment includes a plurality of compartments and where each compartment of the plurality of compartments includes a plurality of conduits arranged in a pattern to provide the at least one marker.

14. A tissue tray according to claim 1, wherein the at least one marker is a visually distinguishable color from a color of the tray material.

15. The tissue tray according to claim 1, wherein the at least one marker comprises a plurality of orientation notches.

16. The tissue tray according to claim 1, wherein the orientation notch is a recess in the upper surface.

17. The tissue tray according to claim 1, wherein the tray further comprises a sidewall extending between and connecting the upper surface and the bottom surface, and the orientation notch is adjacent to and extends from the sidewall.

18. A tissue tray comprising:
   a tray having a material conducive to both radiological analysis and to pathological analysis, the tray comprising an upper surface and a bottom surface, wherein the tray material is a transparent and radiolucent material;
   at least one compartment formed in the upper surface of the tray and recessed toward the bottom surface of the tray, the at least one compartment configured to receive tissue and having one or more fluid conduits passing between openings in the upper and bottom surfaces; and
   at least one marker configured to indicate an orientation of the tray such that the tray is in the same orientation during radiological analysis and pathological analysis, wherein the at least one marker includes a plurality of orientation notches, wherein the tray material is stable with pathological solvents, wherein the tray is configured to be received in a tissue cassette, wherein the at least one compartment includes a plurality of compartments formed in the upper surface of the tray configured to receive tissue, and wherein the tray is configured to preserve orientation of tissue placed therein for correlation of radiologic analysis, tissue fixing, and histo-pathological examination.

19. A tissue tray according to claim 18, wherein the at least one marker includes a visually distinguishable color from a color of the tray material.

20. A tissue examination system comprising:
a tissue cassette having a first side and an opposing second side, the first side having a tray recess therein and an orientation tab extending from the first side; and
a tissue tray configured to be received in the tray recess, the tissue tray including:
- a tray material conducive to both radiological analysis and to pathological analysis, the tissue tray comprising an upper surface and a bottom surface, wherein the tray material is a transparent and radiolucent material;
- at least one compartment formed in the upper surface of the tissue tray configured to receive tissue and having one or more fluid conduits passing between openings in the upper and bottom surfaces; and
- at least orientation notch configured to receive the orientation tab of the tissue cassette and indicate the orientation of the tissue tray such that the tray is in the same orientation during radiological analysis and pathological analysis, and wherein the tray is configured to preserve orientation of tissue placed therein for correlation of radiologic analysis, tissue fixing, and histo-pathological examination.

* * * * *